(12) United States Patent
Govari et al.

(10) Patent No.: US 11,123,135 B2
(45) Date of Patent: Sep. 21, 2021

(54) ENHANCED LARGE-DIAMETER BALLOON CATHETER

(71) Applicant: Biosense Webster (Israel) Ltd., Yokneam (IL)

(72) Inventors: Assaf Govari, Haifa (IL); Christopher Thomas Beeckler, Brea, CA (US); Joseph Thomas Keyes, Sierra Madre, CA (US); Kevin Justin Herrera, West Covina, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 424 days.

(21) Appl. No.: 15/993,471

(22) Filed: May 30, 2018

(65) Prior Publication Data

US 2019/0365464 A1 Dec. 5, 2019

(51) Int. Cl.
*A61B 18/00* (2006.01)
*A61B 18/14* (2006.01)
(Continued)

(52) U.S. Cl.
CPC .......... *A61B 18/1492* (2013.01); *A61B 5/062* (2013.01); *A61M 25/1034* (2013.01);
(Continued)

(58) Field of Classification Search
CPC ........ A61B 18/1492; A61B 2090/3966; A61B 2018/0016; A61B 2018/0022; A61B 18/00357; A61B 2018/00577; A61B 2218/002; A61B 2018/1405; A61B 2018/1465; A61B 2018/00375; A61B 17/22012; A61B 17/2202; A61B 18/12;
(Continued)

(56) References Cited

U.S. PATENT DOCUMENTS 8,641,709 B2   2/2014 Sauvageau et al.
8,777,161 B2 * 7/2014 Pollock ..................... F41H 5/04
                                                244/118.1

(Continued)

FOREIGN PATENT DOCUMENTS

EP      1 790 304 A2   5/2007
EP      3 238 646 A2  11/2017
WO   WO 2011/143468 A2  11/2011

OTHER PUBLICATIONS

Extended European Search Report dated Oct. 29, 2019, Application No. EP 19 17 7365.4.

*Primary Examiner* — Linda C Dvorak
*Assistant Examiner* — Nils A Potter

(57) ABSTRACT

A balloon catheter includes a shaft, a balloon made of an expandable membrane, a flexible substrate, one or more electrodes, and one or more radiopaque flags. The shaft is configured for insertion into a heart of a patient. The balloon is fitted at a distal end of the shaft. The flexible substrate is disposed on the membrane. The one or more electrodes are disposed over the flexible substrate and have a fishbone configuration. The one or more radiopaque flags are coupled to the expandable membrane, wherein the one or more radiopaque flags include a serpentine pattern so that the (Continued)

radiopaque flags fold in conformance with flexible substrate as the expandable membrane is collapsed into a compressed or folded configuration.

11 Claims, 3 Drawing Sheets

(51) Int. Cl.
　　*A61B 5/06*　　　(2006.01)
　　*A61M 25/10*　　(2013.01)
　　*A61B 90/00*　　 (2016.01)

(52) U.S. Cl.
　　CPC .............. *A61B 2018/0016* (2013.01); *A61B 2018/0022* (2013.01); *A61B 2018/00357* (2013.01); *A61B 2018/00577* (2013.01); *A61B 2090/3966* (2016.02); *A61B 2218/002* (2013.01); *A61M 2025/105* (2013.01); *A61M 2025/1031* (2013.01); *A61M 2025/1079* (2013.01)

(58) Field of Classification Search
　　CPC .......... A61B 34/20; A61B 2018/00351; A61B 2018/00595; A61M 25/1034; A61M 2025/1031; A61M 2025/105; A61M 2025/1079
　　USPC ............................................................ 606/41
　　See application file for complete search history.

(56) References Cited

U.S. PATENT DOCUMENTS

| | | | |
|---|---|---|---|
| 8,852,181 B2 | 10/2014 | Malecki et al. | |
| 8,998,893 B2 | 4/2015 | Avitall et al. | |
| 9,345,540 B2 | 5/2016 | Mallin et al. | |
| 9,655,677 B2 | 4/2017 | Salahieh et al. | |
| 9,795,442 B2 | 10/2017 | Salahieh et al. | |
| 2002/0160134 A1 | 10/2002 | Ogushi et al. | |
| 2007/0080322 A1* | 4/2007 | Walba ................ | C09K 19/3804 252/299.01 |
| 2007/0083194 A1 | 4/2007 | Kunis et al. | |
| 2008/0021313 A1* | 1/2008 | Eidenschink ............ | A61F 2/82 600/431 |
| 2008/0202637 A1* | 8/2008 | Hector ................... | C09K 13/04 148/280 |
| 2008/0262489 A1* | 10/2008 | Steinke .............. | A61B 18/1492 606/33 |
| 2010/0114269 A1 | 5/2010 | Wittenberger et al. | |
| 2011/0118632 A1 | 5/2011 | Sinelnikov et al. | |
| 2015/0216650 A1* | 8/2015 | Shaltis ............... | A61B 17/3207 606/200 |
| 2016/0256305 A1* | 9/2016 | Longo ..................... | A61F 2/966 |
| 2017/0042614 A1* | 2/2017 | Salahieh ............ | A61B 18/1492 |
| 2017/0311829 A1 | 11/2017 | Beeckler et al. | |
| 2017/0312022 A1* | 11/2017 | Beeckler ............. | H05K 3/4644 |
| 2020/0008869 A1* | 1/2020 | Byrd ................. | A61B 18/1206 |

* cited by examiner

ENHANCED LARGE-DIAMETER BALLOON CATHETER

FIELD OF THE INVENTION

The present invention relates generally to medical probes, and particularly to balloon catheters.

BACKGROUND OF THE INVENTION

Various known catheter designs have an inflatable ablation balloon fitted at their distal end. For example, U.S. Patent Application Publication 2011/0118632 describes a cardiac ablation device that treats atrial fibrillation by directing and focusing ultrasonic waves into a ring-like ablation region. The ablation device can be steered and positioned without reference to engagement between the device and the pulmonary vein or ostium. In an embodiment, the device is located inside a structural balloon of about 32 mm maximum diameter in the inflated condition.

As another example, U.S. Patent Application Publication 2010/0114269 describes a medical device that may include a catheter body having proximal and distal portions, a fluid injection lumen disposed within elongate body, and a guidewire lumen disposed within the elongate body. A tip portion defining a cavity in fluid communication with the fluid injection lumen may be coupled to the distal end of the guidewire lumen, and an expandable element may be coupled to the distal portion of the catheter body and to the tip portion, such that the expandable element is in fluid communication with the fluid injection lumen. A shaping element may at least partially surround the expandable element, where the shaping element is configurable in a first geometric configuration and a second geometric configuration. The first geometric configuration can include a diameter of approximately 23 mm and the second geometric configuration can include a diameter of approximately 32 mm.

U.S. Patent Application Publication 2017/0312022 describes an irrigated balloon catheter for use in an ostium of a pulmonary vein, which includes a flexible circuit electrode assembly adapted for circumferential contact with the ostium when the balloon is inflated. Adapted for both diagnostic and therapeutic applications and procedures, the balloon catheter may be used with a lasso catheter or focal catheter. The flexible circuit electrode assembly includes a substrate, a contact electrode on an outer surface of the substrate, the contact electrode having a "fishbone" configuration with a longitudinally elongated portion and a plurality of transversal fingers, and a wiring electrode on an inner surface of the substrate, and conductive vias extending through the substrate electrically coupling the contact electrode and the writing electrodes. Microelectrodes with exclusion zones are strategically positioned relative to the electrodes. The electrodes may also be split into electrode portions.

U.S. Patent Application Publication 2002/0160134 describes a balloon catheter having a main-balloon, and a pilot-balloon system that visually indicate the state of the inflation of the main-balloon placed in a human body. The small pilot-balloon is conveniently manufactured by blow molding utilizing substantially the same material and has substantially the same structure as the main balloon. The pilot-balloon is useful for a catheter with balloon or a tube with cuff where the balloon or the cuff is made of a very resilient material. The diameters of the main-balloon and the pilot-balloon at three different inflation pressures were 31 mm and 16 mm at 25 cm $H_2O$, 32 mm and 17 mm at 34 cm $H_2O$, and 34 mm and 18 mm, at 56 cm $H_2O$, respectively.

SUMMARY OF THE INVENTION

We have encountered certain problems designing large diameter balloon catheters with diameters greater than 28 mm. Some of the problems were encountered in compressing such larger size balloon (i.e., "crimped balloon") into a configuration small enough so that the crimped balloon can be transported through the narrow vein (via a catheter of approximately 5 French to approximately 15 French diameters) to the heart during a procedure. We were able to devise various solutions to these problems, which solutions are set forth and illustrated herein this application.

In one approach, we have devised a balloon catheter, including a shaft, a balloon made of an expandable membrane, a flexible substrate, one or more electrodes, and one or more radiopaque flags. The shaft is configured for insertion into a heart of a patient. The balloon is fitted at a distal end of the shaft. The flexible substrate is disposed on the membrane. The one or more electrodes are disposed over the flexible substrate and have a fishbone configuration. The one or more radiopaque flags are coupled to the expandable membrane, wherein the one or more radiopaque flags include a serpentine pattern so that the radiopaque flags fold in conformance with flexible substrate as the expandable membrane is collapsed into a compressed or folded configuration.

In some embodiments, the balloon catheter further includes irrigation pores disposed over the membrane, some of the irrigation pores are distributed over areas covered with the electrodes, and others of the irrigation pores are distributed between the areas covered with the electrodes.

In some embodiments, the radiopaque flags include at least first and second flags that are patterned with different shapes to indicate, when X-ray imaged, an orientation of the balloon catheter.

In an embodiment, the balloon catheter further includes a magnetic position sensor that is disposed proximally to the balloon.

In another embodiment, the balloon catheter further includes a yarn disposed between the membrane and the flexible substrate.

In some embodiments, the yarn is selected from one of an ultra-high molecular weight fiber or a liquid crystal polymer fiber.

In an embodiment, the flexible substrate includes a patterned topography that is configured to increase adhesion of the flexible substrate to the membrane.

There is additionally provided, in accordance with an embodiment of the present invention a method for manufacturing a balloon catheter, the method including providing a shaft that is configured for insertion into a heart of a patient. A distal end of the shaft is fitted with a balloon made of an expandable membrane. A flexible substrate is disposed on the membrane. One or more electrodes having a fishbone configuration are disposed over the flexible substrate. One or more radiopaque flags having a serpentine pattern are disposed over the flexible substrate. The electrodes and the serpentine radiopaque flags are conformed with the membrane in a compressed configuration.

The present invention will be more fully understood from the following detailed description of the embodiments thereof, taken together with the drawings in which:

DETAILED DESCRIPTION OF EMBODIMENTS

Overview

Figure 1:
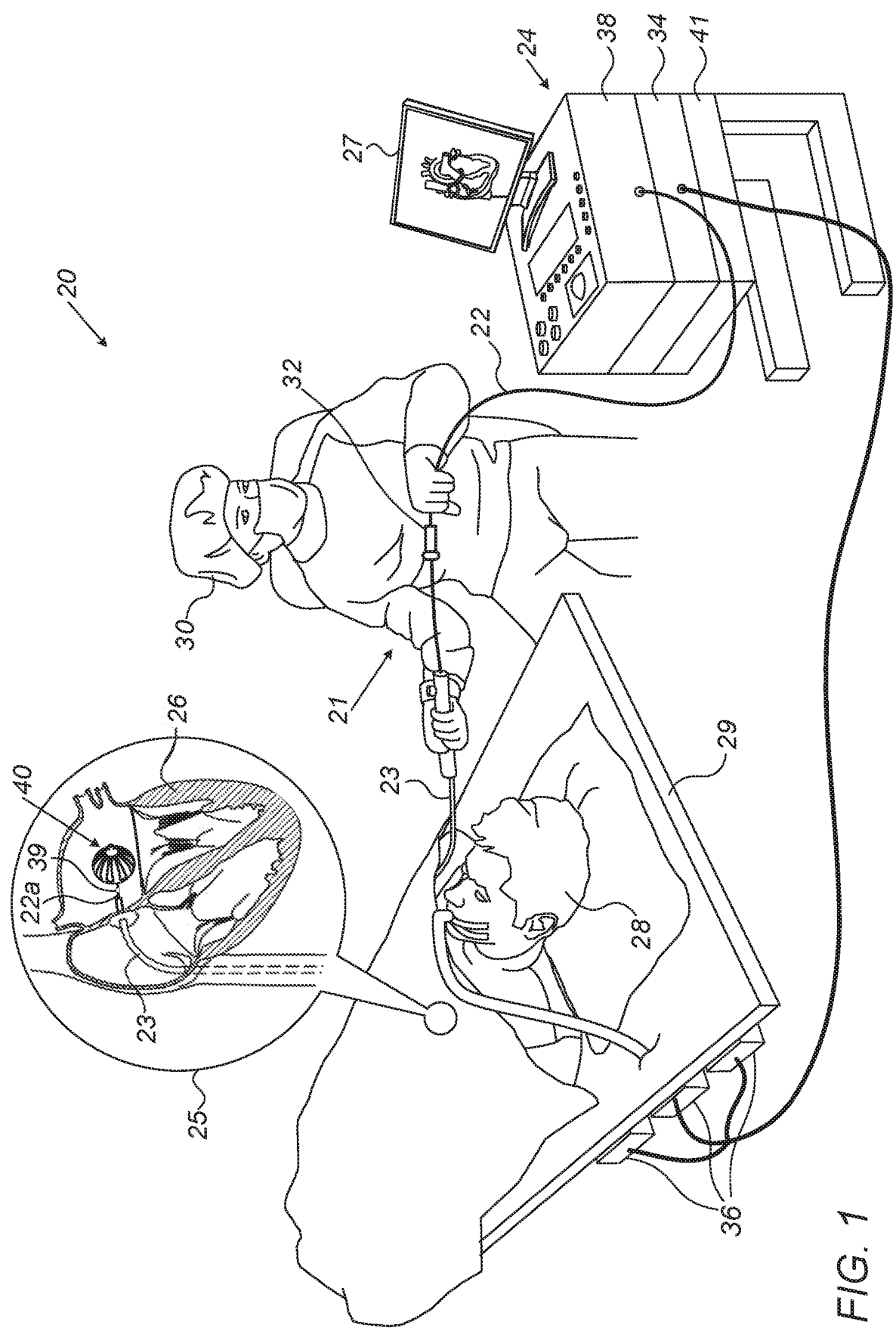
FIG. 1 is a schematic, pictorial illustration of a catheter-based position-tracking and ablation system comprising a Radiofrequency (RF) ablation balloon, in accordance with an embodiment of the present invention.

An expandable ablation balloon may be fitted at a distal end of a catheter that is navigated through the cardiovascular system and inserted into a heart, e.g., for ablating an ostium of a pulmonary vein. The balloon should be large enough so as not to inadvertently enter the vein, but also must be packed in a sufficiently compact form that will allow advancing the balloon through narrow blood vessels. An additional challenge is to ensure safe collapse and retraction of such a balloon back into the catheter sheath in order to remove the balloon from the body after treatment. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Embodiments of the present invention that are described hereinafter enable reliable collapse, and retraction into the sheath, of an ablation balloon with a diameter sufficiently large not to enter a pulmonary vein. In some embodiments, the required balloon diameter, when inflated, is set to approximately 32 millimeters. Elements disposed on the balloon membrane (i.e., wall), such as electrodes and radiopaque flags, are configured to withstand delaminating forces as the balloon collapses, during which the larger membrane stretches and/or develops folds.

In particular, the elements are designed to stretch and/or fold in a conformal manner so as to accommodate stresses that might otherwise cause delamination of the elements from the membrane and/or otherwise prevent sufficient collapsing of the balloon. Additionally or alternatively, at least some of the elements are designed to limit stresses, such as might occur due to overstretching.

One of the elements is a radiopaque flag, which is disposed on a flexible substrate, which itself is attached to the balloon membrane (e.g., glued on an outer surface of the balloon wall). The radiopaque flag, the flexible substrate, and the membrane, are all designed, and are attached to each other, so as to stretch and/or fold together in a manner that allows collapsing the balloon, and safely withdrawing the balloon, into the sheath of the catheter.

In some embodiments, the radiopaque flag is designed with a serpentine pattern to enable the radiopaque flag to stretch and/or fold in a conformal manner (i.e., to fold in conformance with flexible substrate as the expandable membrane is collapsed into a compressed or folded configuration). For the same reason, the flexible substrate comprises a patterned topography, such as a crisscross pattern topography or a matrix or other pattern of blind holes/shapes, which is configured to increase adhesion of the flexible substrate to the balloon membrane, and which, after being glued to the membrane, increases grip area. In this way, the flexible substrate and the membrane stretch and/or fold in a manner conformal with each other, remaining intact when the balloon is collapsed.

In an embodiment of the present invention, one or more radiopaque flags are patterned with shapes to indicate the orientation of the balloon catheter, providing directional and orientation guidance to the operator, as further elaborated below. In some embodiments, a magnetic position sensor is disposed within the catheter shaft, just proximal to the balloon, so that a magnetic position tracking system can assist navigation of the balloon.

In an embodiment, an ablation-electrode, disposed over the flexible substrate, has a fishbone configuration with a longitudinally (i.e., parallel to the distal end of the shaft) elongated portion and a plurality of transversal fingers. This configuration facilitates the stretching and/or folding of the electrode so it will not delaminate during the collapse of the balloon and its retraction back into the sheath.

In some embodiments, irrigation pores are distributed over the membrane. Some of the irrigation pores are distributed over areas covered with the electrodes, while other irrigation pores are distributed between the areas covered with the electrodes. The homogenous distribution of the irrigation pores over the surface of the balloon may ensure more reliable and uniform cooling of tissue and blood during ablation.

The disclosed solutions allow the collapsing of a large balloon into a sufficiently compact form to safely retract the balloon into a catheter sheath, which otherwise may be very hard to achieve, and be potentially unsafe to attempt performing, during a clinical procedure. The disclosed enhanced balloon diameter is large enough to safely ablate an ostium of a pulmonary vein, and afterwards to be safely retracted out of the heart of a patient.

System Description

FIG. 1 is a schematic, pictorial illustration of a catheter-based position-tracking and ablation system 20 comprising an RF ablation balloon 40, in accordance with an embodiment of the present invention. System 20 comprises a catheter 21, wherein, as seen in inset 25, a distal end 22a of shaft 22 of catheter 21 is inserted through a sheath 23 into a heart 26 of a patient 28 lying on a table 29. As further shown in inset 25, distal end 22a comprises a magnetic sensor 39, contained within distal end 22a just proximally to balloon 40.

The proximal end of catheter 21 is connected to a control console 24. In the embodiment described herein, catheter 21 may be used for any suitable therapeutic and/or diagnostic purpose, such as electrical sensing and/or ablation of tissue in heart 26.

During navigation of distal end 22a in heart 26, console 24 receives signals from magnetic sensor 39 in response to magnetic fields from external field generators 36, for example, for the purpose of measuring the position of ablation balloon 40 in the heart and, optionally, presenting the tracked position on a display 27. Magnetic field generators 36 are placed at known positions external to patient 28, e.g., below patient table 29. Console 24 also comprises a driver circuit 34, configured to drive magnetic field generators 36.

In an embodiment, position signals received from position sensor 39 are indicative of the position of ablation balloon 40 in the coordinate system of position tracking and ablation system 20. The method of position sensing using external magnetic fields is implemented in various medical applications, for example, in the CARTO™ system, produced by Biosense-Webster Inc. (Irvine, Calif.), and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Physician 30 navigates the distal end of shaft 22 to a target location in heart 26 by manipulating shaft 22 using a manipulator 32 near the proximal end of the catheter and/or deflection from the sheath 23. During the insertion of shaft 22, balloon 40 is maintained in a collapsed configuration by sheath 23. By containing balloon 40 in a collapsed configuration, sheath 23 also serves to minimize vascular trauma along the way to target location.

Control console 24 comprises a processor 41, typically a general-purpose computer, with suitable front end and interface circuits 38 for receiving signals from catheter 21, as well as for applying treatment via catheter 21 in heart 26 and for controlling the other components of system 20. Processor 41 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

The example configuration shown in FIG. 1 is chosen purely for the sake of conceptual clarity. The disclosed techniques may similarly be applied using other system components and settings. For example, system 20 may comprise other components and perform non-cardiac ablative treatments.

Enhanced Large Diameter Balloon Catheter

Figure 2:
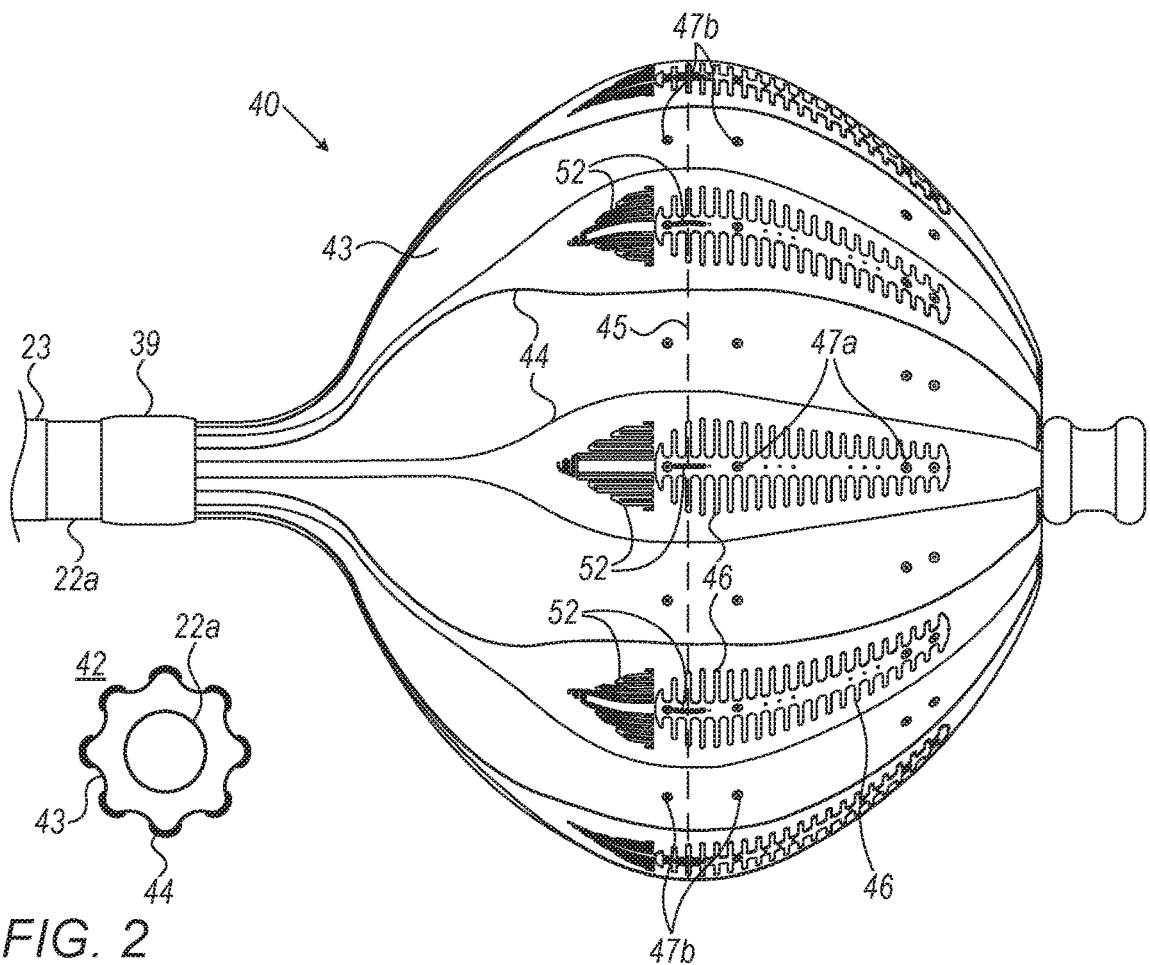
FIG. 2 is a schematic pictorial illustration of the balloon catheter from FIG. 1, in accordance with an embodiment of the present invention.

FIG. 2 is a schematic pictorial illustration of balloon catheter 40 from FIG. 1, in accordance with an embodiment of the present invention. As seen, balloon 40 is fitted at distal end 22a (of shaft 22) that protrudes from sheath 23. Magnetic position sensor 39 is contained within distal end 22a just proximally to balloon 40. Expandable balloon 40 has an exterior wall or membrane 43 of a bio-compatible material, for example, formed from a plastic such as polyethylene terephthalate (PET), polyurethane or PEBAX. Ablation-electrodes 46 are disposed in circumference over balloon 40, on flexible substrates 44.

Balloon 40 has a distal end and a proximal end defining a longitudinal axis. In some embodiments, balloon 40 is expanded and contracted (i.e., collapsed) using a "balloon advancer" rod (not shown). The rod may be extended outwardly from shaft 22 to longitudinally elongate balloon 40 into an oblong shape. It may be withdrawn to provide the balloon with a spherical shape. The balloon advancer rod is the primary mechanism for changing the shape of balloon between spherical and oblong configurations, while filling the balloon with saline further tightens the skin of the balloon to the spherical shape.

In some embodiments balloon 40 comprises irrigation pores 47a and 47b, through which saline solution is irrigated for cooling tissue and blood during ablation. Pores 47a are located in areas covered by electrodes 46, whereas pores 47b are located over membrane 43 between areas covered by electrodes 46.

In some embodiments, radiopaque flags 52 are patterned in different serpentine shapes. In an embodiment of the present invention, the differently shaped radiopaque flags 52 provide orientation and directional guidance, as further elaborated below. An electrophysiology catheter disposed with two or more radiopaque markers having distinct forms of each other is described in U.S. patent application Ser. No. 15/939,154, filed Mar. 28, 2018, entitled "Irrigated Electrophysiology Catheter with Distinguishable Electrodes for Multi-Electrode Identification and Orientation Under 2-D Visualization," which is assigned to the assignee of the present patent application and whose disclosure is incorporated herein by reference.

The diameter of balloon 40, when inflated, is defined by an equator 45 over the exterior of membrane 43, wherein the equator lies in a plane perpendicular to the axis of distal end 22a. In some embodiments, when inflated, the balloon equatorial diameter (i.e., the diameter of equator 45) measures approximately thirty-two millimeters.

An inset 42 of FIG. 2 shows a cross sectional view of balloon 40 in a collapsed state (e.g., ready to be retracted into sheath 23). As seen in inset 42, when the balloon is collapsed, membrane 43 and flexible substrate 44, while mainly stretched as elongated by the extender rod, may still develop folds. Such folds put stress on flexible substrate 44, or on elements disposed over flexible substrate 44, which might result in delamination. As balloon diameter increases, more pronounced folding may occur as the balloon is forcibly collapsed, thus increasing the delaminating forces. Moreover, if some disposed elements are too rigid, either axially or transversely, they may hinder collapsing the balloon sufficiently to retract it safely into sheath 23. In some embodiments of the present invention, elements disposed on the membrane are designed so they, and the membrane, will axially stretch and/or transversely fold in a mutually conformal manner, as explained in the detailed description of FIG. 3, so as to avoid the problems described above.

An irrigated balloon ablation catheter is described in U.S. Publication No. 2017/0312022, titled "Irrigated balloon catheter with flexible circuit electrode assembly," the entire content of which is incorporated herein by reference.

The example illustration shown in FIG. 2 is chosen purely for the sake of conceptual clarity. Other sizes of balloon 40 and various configurations of its components, such as of ablation-electrodes 46, are possible. When inflated, the equatorial diameter of balloon 40 can be larger or smaller than thirty-two millimeters.

Figure 3:
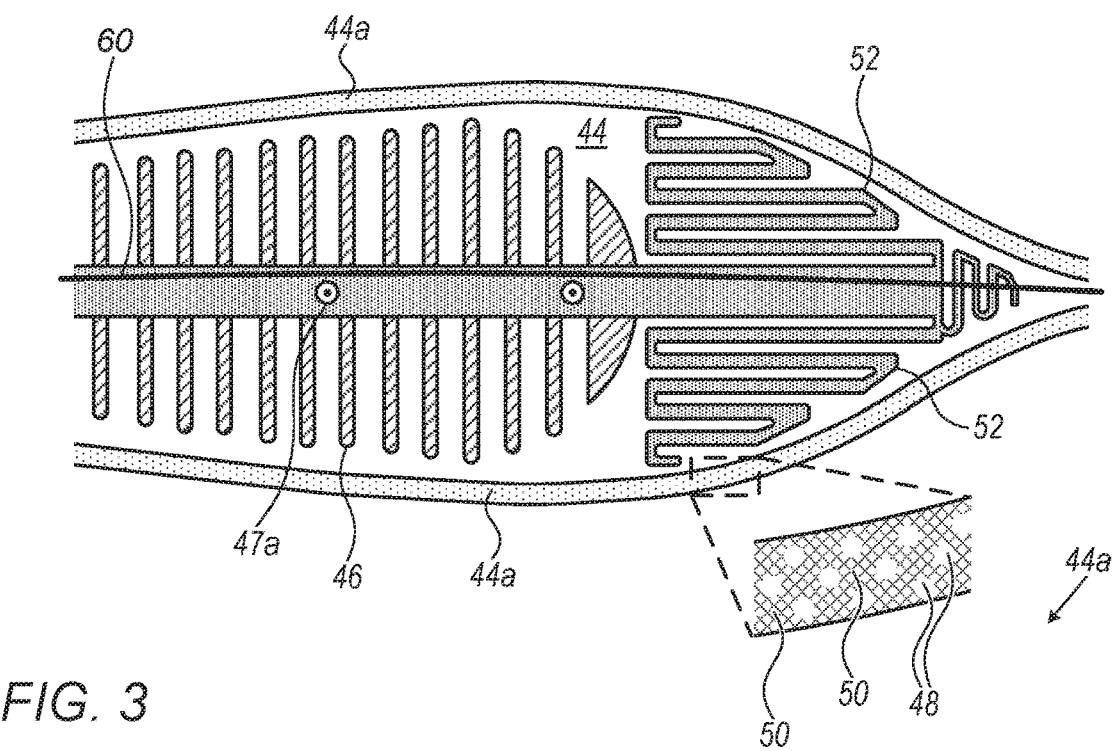
FIG. 3 is a detailed schematic pictorial top view of a flexible circuit electrode assembly, in accordance with an embodiment of the present invention.

FIG. 3 is a detailed schematic pictorial top view of a flexible circuit electrode assembly, in accordance with an embodiment of the present invention. In an embodiment, an ablation electrode 46 has a form of a "fishbone," advantageously increasing the circumferential or equatorial contact surface of electrode 46 with tissue. At the same time, a fishbone form more easily stretches and/or folds in a conformal manner so as to allow the collapse of balloon 40 into a sufficiently tight form about distal end 22a.

As seen in FIG. 3, radiopaque flags or markers 52 are patterned in serpentine shapes, in order to allow radiopaque flags 52 to fold in a manner conformal with flexible substrate 44 as balloon 40 is collapsed. Also seen are irrigation pores 47a, which are located in areas not covered by electrodes 46.

In an embodiment, a yarn or fiber 60 made of Liquid Crystal Polymer (LCP) such as, for example, Vectran® or Ultra High Molecular Weight Polyethylene (UHMWPE) such as, for example, Dyneema®, runs between membrane 43 and flexible substrate 44 from one end of flexible substrate 44 to the other. Due to the high elastic modulus of yarn 60, the yarn or fiber limits any axial stretch, while balloon 40 collapses, that might otherwise cause delamination. The yarn also prevents tearing of the flexible substrate 44 at its narrow distal tail, which does not have any metal to limit the elongation. The yarn allows the application of significant distal force with a balloon advancer rod on the lumen (by surrounding membrane 43), so as to evacuate the internal saline solution without risk of damaging any electrical circuits attached to flexible substrate 44.

A zoom-in on an edge area 44a of flexible substrate 44 shows a crisscross pattern 50 topography (i.e., "waffle" pattern) put into edge area 44a to increase adhesion of flexible substrate 44 to membrane 43, after flexible substrate 44 is glued to membrane 43. The waffle pattern provides the necessary adhesion by increasing grip area for the adhesive, which both strengthens the bond and withstands delaminating forces acting on substrate 44 that occur as balloon 40 is collapsed for retraction into sheath 23. As is further seen in FIG. 3, in a zoom-in on flexible substrate 44, a plurality of perforations 50 is patterned, wherein perforations 50 are configured to receive an adhesive for affixing the substrate 44 to the membrane 43.

The example top view shown in FIG. 3 is chosen purely for the sake of conceptual clarity. Other materials may be used, for example, yarn 60 may be made of a para-aramid. In an alternative embodiment for radiopaque flags 52, seen in FIG. 4, a different solution to withstanding delamination is exemplified, as explained below.

Figure 4:
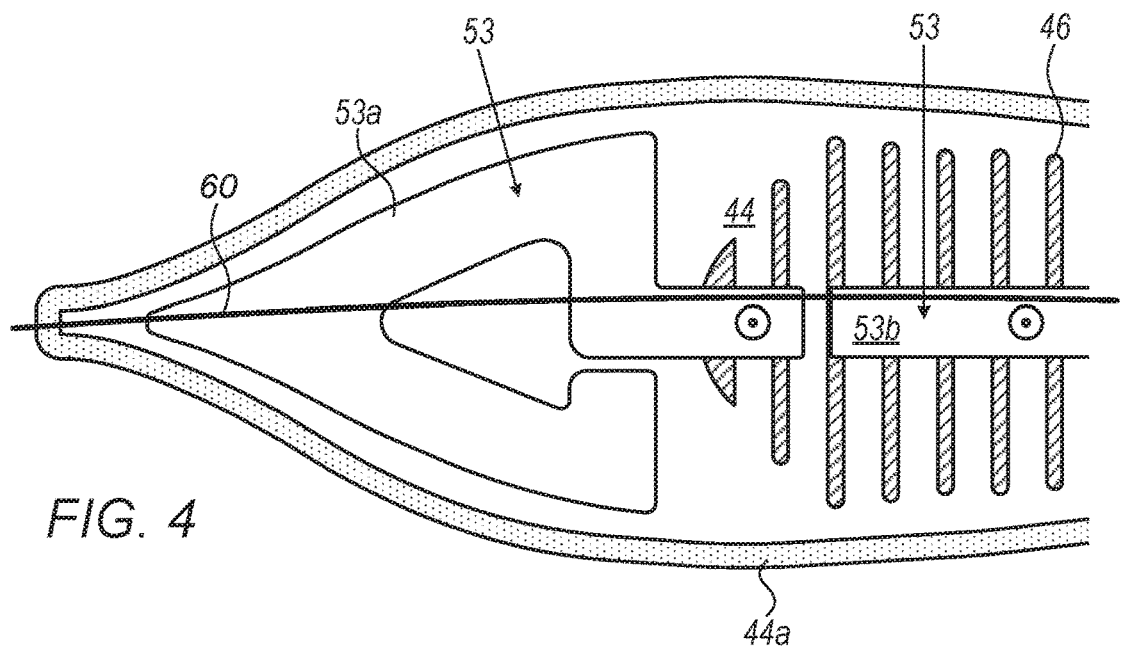
FIG. 4 is a pictorial top view of the flexible circuit electrode assembly, in accordance with another embodiment of the present invention.

FIG. 4 is a pictorial top view of the flexible circuit electrode assembly, in accordance with another embodiment of the present invention. As seen, a radiopaque flag 53 is split into radiopaque flags 53a and 53b, in order to allow the radiopaque flags to stretch more easily in the longitudinal direction. Additionally, radiopaque flag 53a has a form of a voided triangle, to indicate an orientation when imaged by X-ray.

Figure 5:
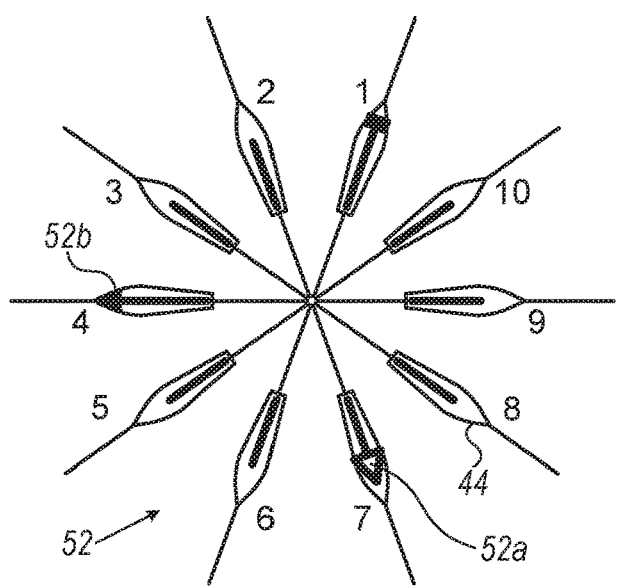
FIG. 5 is a schematic pictorial top view of a spatial arrangement of radiopaque flags, in accordance with an embodiment of the present invention.

FIG. 5 is a schematic pictorial top view of the spatial arrangement of radiopaque flags 52, in accordance with an embodiment of the present invention. Light gray outlines of flexible substrates 44 can also be seen. To indicate an orientation, some of the ten shown radiopaque flags 52 are patterned with unique features. As shown in FIG. 5, radiopaque flags 52 (seen numbered 1 to 10) can be divided into a first type and a second type of flags. Flags of a first type, such as flag 52a, have a distinct feature. Flags of a second type are identical one with the other, e.g., all comprising a plain line. Flags 52 are designed this way to indicate to physician 30 an orientation of electrodes 46, and, in that way, of balloon 40 as a whole, inside a chamber of heart 26. For example, radiopaque flag 52a includes the pattern of a hollow arrow, while radiopaque flag 52b includes a pattern of full arrow.

The example shown in FIG. 5 is chosen purely for the sake of conceptual clarity. Other patterns may be designed and used. The number and the arrangement of uniquely patterned radiopaque flags in FIG. 5 is brought by way of example, and may generally vary.

Figure 6:
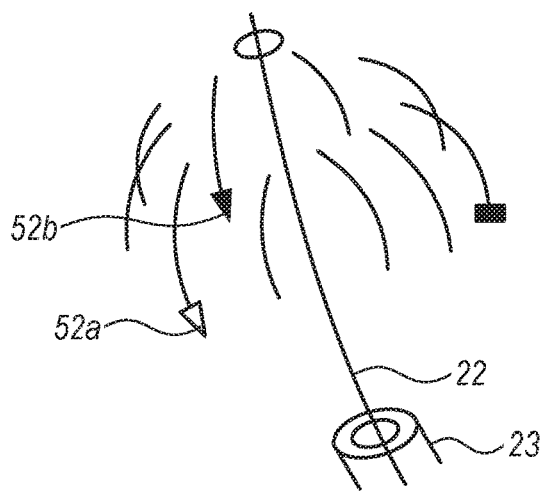
FIG. 6 is a pictorial volume rendering of radiopaque flags on a balloon, as would be seen with X-ray imaging, in accordance with an embodiment of the present invention.

FIG. 6 is a pictorial volume rendering of radiopaque flags 52 on a balloon, as would be seen with X-ray imaging, in accordance with an embodiment of the present invention. As FIG. 6 shows, an X-ray image of balloon 40 may resolve radiopaque flags 52a and 52b to indicate to physician 30 a sense of spatial orientation of balloon 40.

Although the embodiments described herein mainly address cardiac balloon catheters, the methods and systems described herein can also be used in other applications, such as in otolaryngology or neurology procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A balloon catheter, comprising:
   a shaft configured for insertion into a heart of a patient;
   a balloon made of an expandable membrane, which is fitted at a distal end of the shaft;
   ten flexible substrates, which are disposed on the membrane radially about a center of the balloon;
   ten electrodes, which are disposed over each of the respective ten flexible substrates; and
   first, second, third, fourth, fifth, sixth, seventh, eighth, ninth and tenth radiopaque flags disposed on respective ten flexible substrates, the first, fourth and seventh radiopaque flags comprising three respective shapes different from an identical shape of the second, third, fifth, sixth, eighth, ninth and tenth radiopaque flags,
   wherein the first radiopaque flag comprises a shape different from a shape of the fourth radiopaque flag and a shape of the seventh radiopaque flag, and the fourth radiopaque flag comprises a shape different from a shape of the seventh radiopaque flag, each of the flags include a serpentine pattern so that the radiopaque flags fold in conformance with flexible substrate as the expandable membrane is collapsed into a compressed or folded configuration.

2. The balloon catheter according to claim 1, and further comprising irrigation pores disposed over the membrane, wherein some of the irrigation pores are distributed over areas covered with the electrodes, and others of the irrigation pores are distributed between the areas covered with the electrodes.

3. The balloon catheter according to claim 1, and further comprising a magnetic position sensor that is disposed proximally to the balloon.

4. The balloon catheter according to claim 1, and further comprising a yarn disposed between the membrane and the flexible substrate.

5. The balloon catheter according to claim 4, wherein the yarn is selected from one of an ultra-high molecular weight fiber or a liquid crystal polymer fiber.

6. The balloon catheter according to claim 1, wherein the flexible substrate comprises a patterned topography that is configured to increase adhesion of the flexible substrate to the membrane.

7. A method for manufacturing a balloon catheter, the method comprising:

provrviding a shaft that is configured for insertion into a heart of a patient;

fitting, at a distal end of the shaft, a balloon made of an expandable membrane;

disposing on the membrane ten separate flexible substrates disposed radially about a center of the balloon;

disposing over the respective ten flexible substrates ten separate electrodes having a fishbone configuration;

disposing over the flexible substrate first, second, third, fourth, fifth, sixth, seventh, eight, ninth and tenth radiopaque flags, in which the first, fourth and seventh radiopaque flags comprise three respective shapes different from identical shape of the second, third, fifth, sixth, eighth, ninth and tenth radiopaque flags, and further in which the first radiopaque flags includes a shape different from a shape of the fourth radiopaque flag and a shape of the seventh radiopaque flag, and the fourth radiopaque flag comprises a shape different from a shape of the seventh radiopaque flag; and conforming the electrodes and serpentine radiopaque flags with the membrane in a compressed configuration.

8. The method according to claim 7, and further comprising disposing irrigation pores over the membrane, wherein some of the irrigation pores are distributed over areas covered with the electrodes, and others of the irrigation pores are distributed between the areas covered with the electrodes.

9. The method according to claim 7, and further comprising disposing a magnetic position sensor proximally to the balloon.

10. The method according to claim 7, and further comprising disposing a yarn between the membrane and the flexible substrate.

11. The method according to claim 7, and further comprising increasing adhesion of the flexible substrate to the membrane by including a patterned topography in the flexible substrate.

* * * * *